(12) United States Patent
Ray et al.

(10) Patent No.: US 7,625,507 B2
(45) Date of Patent: Dec. 1, 2009

(54) EXTRUSION PROCESS FOR FORMING CHEMICALLY STABLE DRUG MULTIPARTICULATES

(75) Inventors: Roderick J. Ray, Bend, OR (US); Leah E. Appel, Bend, OR (US); David D. Newbold, Bend, OR (US); Dwayne T. Friesen, Bend, OR (US); Scott B. McCray, Bend, OR (US); David K. Lyon, Bend, OR (US); James B. West, Bend, OR (US); Marshall D. Crew, Bend, OR (US); Joshua R. Shockey, Bend, OR (US)

(73) Assignee: Pfizer Inc., New York, NY (US)

( * ) Notice: Subject to any disclaimer, the term of this patent is extended or adjusted under 35 U.S.C. 154(b) by 331 days.

(21) Appl. No.: 11/004,165

(22) Filed: Dec. 3, 2004

(65) Prior Publication Data

US 2005/0181061 A1 Aug. 18, 2005

Related U.S. Application Data

(60) Provisional application No. 60/527,315, filed on Dec. 4, 2003.

(51) Int. Cl.
*B29B 9/00* (2006.01)

(52) U.S. Cl. .................. 264/5; 264/8; 264/9; 264/10; 264/11

(58) Field of Classification Search ............... None
See application file for complete search history.

(56) References Cited

U.S. PATENT DOCUMENTS

| | | | |
|---|---|---|---|
| 2,064,121 A | 9/1903 | Patel et al. | |
| 2,955,956 A | 10/1960 | Baugh et al. | 117/100 |
| 4,053,264 A | 10/1977 | King | 425/8 |
| 4,086,346 A | 4/1978 | Bocker et al. | 424/253 |
| 4,092,089 A | 5/1978 | Bocker et al. | 425/10 |
| 4,293,570 A | 10/1981 | Vadasz | 426/3 |
| 4,474,768 A | 10/1984 | Bright | 424/180 |
| 4,517,359 A | 5/1985 | Kobrehel et al. | 536/7.4 |
| 4,675,140 A | 6/1987 | Sparks et al. | 264/4.3 |
| 4,874,611 A | 10/1989 | Wilson et al. | 424/410 |
| 4,931,285 A | 6/1990 | Edgren et al. | 424/473 |
| 4,957,681 A | 9/1990 | Klimesch et al. | 264/211.23 |
| 4,963,531 A | 10/1990 | Remington | 514/29 |
| 5,019,302 A | 5/1991 | Sparks et al. | 264/8 |
| 5,024,842 A | 6/1991 | Edgren et al. | 424/473 |
| 5,047,244 A | 9/1991 | Sanvordeker et al. | 424/435 |
| 5,064,650 A | 11/1991 | Lew | 424/435 |
| 5,084,287 A | 1/1992 | Ghebre-Sellassie et al. | 424/495 |
| 5,100,592 A | 3/1992 | Sparks et al. | 264/7 |
| 5,143,662 A | 9/1992 | Chesterfield et al. | 264/8 |
| 5,160,743 A | 11/1992 | Edgren et al. | 424/473 |
| 5,169,645 A | 12/1992 | Shukla et al. | 424/499 |
| 5,183,690 A | 2/1993 | Carr et al. | 427/213.31 |
| 5,194,262 A | 3/1993 | Goldberg et al. | 424/401 |
| 5,196,199 A | 3/1993 | Fuisz | 424/401 |
| 5,213,810 A | 5/1993 | Steber | 424/490 |
| 5,236,734 A | 8/1993 | Fuisz | 426/641 |
| 5,292,657 A | 3/1994 | Rutherford et al. | 435/243 |
| 5,348,758 A | 9/1994 | Fuisz et al. | 426/660 |
| 5,380,473 A | 1/1995 | Bogue et al. | 264/11 |
| 5,405,617 A | 4/1995 | Gowan, Jr. et al. | 424/464 |
| 5,407,676 A | 4/1995 | Fuisz | 424/401 |
| 5,429,836 A | 7/1995 | Fuisz | 426/601 |
| 5,433,951 A | 7/1995 | Serajuddin et al. | 424/486 |
| 5,456,932 A | 10/1995 | Fuisz et al. | 426/548 |
| 5,461,089 A | 10/1995 | Handyside et al. | 523/171 |
| 5,500,162 A | 3/1996 | Theisen et al. | 264/9 |
| 5,501,858 A | 3/1996 | Fuisz | 424/439 |
| 5,505,983 A | 4/1996 | Kamada | 427/2.21 |
| 5,518,730 A | 5/1996 | Fuisz | 424/426 |
| 5,539,000 A | 7/1996 | Leonard | 514/682 |
| 5,549,917 A | 8/1996 | Cherukuri et al. | 426/96 |
| 5,556,652 A | 9/1996 | Cherukuri et al. | 426/5 |
| 5,569,467 A | 10/1996 | Ruiz | 424/489 |
| 5,582,855 A | 12/1996 | Cherukuri | 426/5 |
| 5,597,416 A | 1/1997 | Fuisz et al. | 127/30 |
| 5,597,844 A | 1/1997 | Chauhan et al. | 514/400 |
| 5,601,761 A | 2/1997 | Hoffman et al. | 264/4.3 |
| 5,605,889 A | 2/1997 | Curatolo et al. | 514/29 |
| 5,633,006 A | 5/1997 | Catania et al. | 424/441 |
| 5,683,720 A | 11/1997 | Myers et al. | 424/489 |

(Continued)

FOREIGN PATENT DOCUMENTS

EP 0080341 6/1983

(Continued)

OTHER PUBLICATIONS

Savolainen, Marja et al., International Journal of Pharmaceutics, Aug. 27, 2003, vol. 262, No. 1-2., pp. 47-62, "Evaluation of polar lipid-hydrophilic polymer microparticles."

(Continued)

*Primary Examiner*—Mary Lynn F Theisen
(74) *Attorney, Agent, or Firm*—Chernoff, Vilahuer, McClung & Stenzel, LLP

(57) ABSTRACT

Reduced levels of drug degradation in drug-containing multiparticulates are obtained by an extrusion/melt-congeal process.

19 Claims, No Drawings

U.S. PATENT DOCUMENTS

| | | | | |
|---|---|---|---|---|
| 5,690,959 | A | 11/1997 | Palepu et al. | 424/472 |
| 5,705,190 | A | 1/1998 | Broad et al. | 424/465 |
| 5,707,646 | A | 1/1998 | Yajima et al. | 424/439 |
| 5,733,577 | A | 3/1998 | Myers et al. | 424/488 |
| 5,741,519 | A | 4/1998 | Rosenberg et al. | 424/464 |
| 5,744,180 | A | 4/1998 | Cherukuri et al. | 426/99 |
| 5,747,058 | A | 5/1998 | Tipton et al. | 424/423 |
| 5,766,521 | A | 6/1998 | Le Thiesse et al. | 264/7 |
| 5,792,474 | A | 8/1998 | Rauchfuss | 424/489 |
| 5,824,342 | A | 10/1998 | Cherukuri et al. | 424/484 |
| 5,840,334 | A | 11/1998 | Raiden et al. | 424/464 |
| 5,849,223 | A | 12/1998 | Myers et al. | 264/15 |
| 5,851,553 | A | 12/1998 | Myers et al. | 424/488 |
| 5,851,555 | A | 12/1998 | Sanghvi et al. | 424/464 |
| 5,855,915 | A | 1/1999 | Pinkus | 242/486 |
| 5,869,098 | A | 2/1999 | Misra et al. | 424/484 |
| 5,869,101 | A | 2/1999 | Moller et al. | 424/489 |
| 5,883,103 | A | 3/1999 | Burnside et al. | 514/262 |
| 5,891,845 | A | 4/1999 | Myers | 514/11 |
| 5,912,030 | A | 6/1999 | Huzinec et al. | 426/3 |
| 5,919,489 | A | 7/1999 | Saleki-Gerhardt et al. | 424/501 |
| 5,935,600 | A | 8/1999 | Cherukuri et al. | 424/464 |
| 5,948,407 | A | 9/1999 | McGuinness et al. | 424/184.1 |
| 5,952,004 | A | 9/1999 | Rudnic et al. | 424/455 |
| 5,958,452 | A | 9/1999 | Oshlack et al. | 424/457 |
| 5,965,161 | A | 10/1999 | Oshlack et al. | 424/457 |
| 5,965,164 | A | 10/1999 | Fuisz et al. | 424/489 |
| 5,972,373 | A | 10/1999 | Yajima et al. | 424/439 |
| 5,980,941 | A | 11/1999 | Raiden et al. | 424/464 |
| 6,010,718 | A | 1/2000 | Al-Razzak et al. | 424/464 |
| 6,013,280 | A | 1/2000 | Frisbee et al. | 424/464 |
| 6,048,541 | A | 4/2000 | Misra et al. | 424/401 |
| 6,051,253 | A | 4/2000 | Zettler et al. | 424/465 |
| 6,068,859 | A | 5/2000 | Curatolo et al. | 424/490 |
| 6,074,580 | A * | 6/2000 | Le Thiesse et al. | 264/14 |
| 6,077,541 | A | 6/2000 | Chen et al. | 424/480 |
| 6,083,430 | A | 7/2000 | Fuisz et al. | 264/5 |
| 6,086,920 | A | 7/2000 | Frisbee et al. | 424/489 |
| 6,090,830 | A | 7/2000 | Myers et al. | 514/356 |
| 6,103,264 | A | 8/2000 | Hoffmann et al. | 424/468 |
| 6,117,452 | A | 9/2000 | Ahlgren et al. | 424/468 |
| 6,139,872 | A | 10/2000 | Walsh | 424/464 |
| 6,165,512 | A | 12/2000 | Mezaache et al. | 424/489 |
| 6,221,368 | B1 | 4/2001 | Breitenbach et al. | 424/400 |
| 6,245,903 | B1 | 6/2001 | Karimian et al. | 536/7.4 |
| 6,248,363 | B1 | 6/2001 | Patel et al. | 424/497 |
| 6,261,599 | B1 | 7/2001 | Oshlack et al. | 424/457 |
| 6,268,489 | B1 | 7/2001 | Allen et al. | 536/7.4 |
| 6,270,804 | B1 | 8/2001 | Getz et al. | 424/490 |
| 6,328,993 | B1 | 12/2001 | Linder et al. | 424/451 |
| 6,335,033 | B2 | 1/2002 | Oshlack et al. | 424/457 |
| 6,365,574 | B2 | 4/2002 | Singer et al. | 514/29 |
| 6,383,510 | B1 | 5/2002 | Linder et al. | 424/438 |
| 6,387,401 | B2 * | 5/2002 | Rosenberg et al. | 424/464 |
| 6,395,300 | B1 | 5/2002 | Straub et al. | 424/489 |
| 6,423,345 | B2 | 7/2002 | Bernstein et al. | 424/501 |
| 6,500,459 | B1 | 12/2002 | Chhabra et al. | 424/474 |
| 6,551,616 | B1 | 4/2003 | Notario et al. | 424/464 |
| 6,569,463 | B2 | 5/2003 | Patel et al. | 424/497 |
| 6,576,258 | B1 | 6/2003 | Kofler et al. | 424/458 |
| 6,645,528 | B1 | 11/2003 | Straub et al. | 424/489 |
| 6,682,759 | B2 | 1/2004 | Lim et al. | 424/468 |
| 6,689,390 | B2 | 2/2004 | Bernstein et al. | 424/501 |
| 6,692,767 | B2 | 2/2004 | Burnside et al. | 424/489 |
| 2001/0003590 | A1 | 6/2001 | Joachim et al. | 424/465 |
| 2001/0006650 | A1 | 7/2001 | Burnside et al. | 424/400 |
| 2002/0009433 | A1 | 1/2002 | Curatolo et al. | 424/94.1 |
| 2002/0025342 | A1 | 2/2002 | Linder et al. | 424/489 |
| 2002/0044968 | A1 | 4/2002 | Van Lengerich | 424/469 |
| 2003/0091626 | A1 * | 5/2003 | Katsuta | 424/465 |
| 2003/0165563 | A1 | 9/2003 | Murphy et al. | 424/465 |
| 2003/0186952 | A1 * | 10/2003 | Crew et al. | 514/177 |
| 2003/0190365 | A1 | 10/2003 | Fergione et al. | 424/489 |
| 2003/0228357 | A1 | 12/2003 | Johnson et al. | 424/465 |
| 2004/0014951 | A1 | 1/2004 | Dumic et al. | 536/7.1 |
| 2004/0023898 | A1 | 2/2004 | Dunne | |
| 2004/0121003 | A1 | 6/2004 | Chickering, III et al. | 424/465 |
| 2005/0026851 | A1 | 2/2005 | Danilovski et al. | 514/28 |

FOREIGN PATENT DOCUMENTS

| | | |
|---|---|---|
| EP | 0109253 | 5/1984 |
| EP | 0582396 | 2/1994 |
| EP | 0925789 | 6/1999 |
| EP | 0943341 | 9/1999 |
| EP | 0776658 | 2/2000 |
| EP | 1127580 | 8/2001 |
| GB | 2066070 | 7/1981 |
| GB | 2091097 | 7/1982 |
| IN | 187487 | 5/2000 |
| WO | WO9107171 | 5/1991 |
| WO | WO9400112 | 1/1994 |
| WO | WO9427557 | 12/1994 |
| WO | WO9509601 | 4/1995 |
| WO | WO9806714 | 2/1998 |
| WO | WO9818610 | 5/1998 |
| WO | WO9846239 | 10/1998 |
| WO | WO9856357 | 12/1998 |
| WO | WO9903453 | 1/1999 |
| WO | WO9924031 | 5/1999 |
| WO | WO0026285 | 5/2000 |
| WO | WO0057886 | 10/2000 |
| WO | WO0142221 | 6/2001 |
| WO | WO0178688 | 10/2001 |
| WO | WO0185135 | 11/2001 |
| WO | WO0224174 | 3/2002 |
| WO | WO02064121 | 8/2002 |
| WO | WO03018031 | 3/2003 |
| WO | WO03032922 | 4/2003 |
| WO | WO03037304 | 5/2003 |
| WO | WO03053402 | 7/2003 |
| WO | WO0363834 | 8/2003 |
| WO | WO03063832 | 8/2003 |
| WO | WO03063833 | 8/2003 |
| WO | WO03068191 | 8/2003 |
| WO | WO03105810 | 12/2003 |
| WO | WO2004000865 | 12/2003 |
| WO | WO2004009608 | 1/2004 |
| WO | WO2004035063 | 4/2004 |
| WO | WO2004087096 | 10/2004 |

OTHER PUBLICATIONS

Foulds, G., et al., "The effects of an antacid or cimetidine on the serum concentrations of azithromycin", J. Clin. Pharmacol. Feb 1991; 31(2): 164-7 (Abstract).

Amsden, G.W., et al., "Serum and WBC pharmacokinetics of 1500 mg of azithromycin when given either as a single dose or over a 3 day period in healthy volunteers", J. Antimicrobial Chemotherapy (2001), 47(1), 61-66 (Abstract).

Zithromax® azithromycin tablet 250 mg, Quantitative Composition of the Tablet Blend.

Zithromax® azithromycin for oral suspension composition 200 mg/5mL, 200mg/5mL Drug Product.

Zithromax® azithromycin for oral suspension composition 1 gram sachet, Quantitative Composition of the Drug Product.

Zithromax® azithromycin for oral suspension composition 100 mg/5mL, Quantitative Compositions of the Drug Products.

Zithromax® (azithromycin tablets and azithromycin for oral suspension), Full U.S. Prescribing Information, 70-5179-00-4.

Zithromax® (azithromycin capsules) (azithromycin tablets) and (azithromycin for oral suspension), Full U.S. Prescribing Information, 69-4763-00-9.

Food and Drug Administration Center for Drug Evaluation and Research Approved Drug Products with Therapeutic Evaluations, 24th Edition, Orange Book Listings of Azithromycin Dosage Forms.

Barber, J., "Assignments of the $^{13}$C and $_1$H NMR Spectra of Azithromycin in CDCl$_3$," *Magnetic Resonance in Chemistry* 29:7(1991)740-743.

Barthelemy, P., et al., "Compritol® 888 ATO: An Innovative Hot-Melt Coating Agent for Prolonged-Release Drug Formulations," *Europ. J. Pharmaceut and Biopharmaceutics*, 47(1999)87-90.

Bhagwatwar, H., et al., "Preparation of Drug-Containing Wax Microspheres Using a Melt Dispersion Technique," *Pharmaceutical Research*, 6:7(1989)S-177, Abstract No. PD 1201.

Breitenbach, J., et al., "Solid Dispersions by an Integrated Melt Extrusion System," *Proceed. Int'l Symp. Control. Re. Bioact. Materials*, 25(1998)804-805.

Craig, D.Q.M., "The Physical Characterisation of Gelucire 50/13," *Bulletin Technique Gattefosse*, 89(1998)39-51.

DeMan, J.M., et al., "Thermal Analysis Microscopy for the Study of Phase Changes in Fats," *Food Microstructure*, 4(1985)233-239.

Eldem T., et al., "Polymorphic Behavior of Sprayed Lipid Micropellets and Its Evaluation by Differential Scanning Calorimetry and Scanning Electron Microscopy;" *Pharmaceutical Research*, 8:2(1991)178-184.

Eldem, T., et al., "Optimization of Spray-Dried and—Congealed Lipid Micropellets and Characterization of Their Surface Morphology by Scanning Electron Microscopy," Pharmaceutical Research, 8:1(1991)47-54.

Emas, M., and H. Nyqvist, "Methods of Studying Aging and Stabilization of Spray-Congealed Solid Dispersions with Carnauba Wax. 1. Microcalorimetric Investigation," *Int'l J. Pharmaceutics*, 197(2000)117-127.

Faham, A., et al., "Hot-Melt Coating Technology. I. Influence of Compritol 888 Ato and Granule Size on Theophylline Release," *Drug Dev. Industrial Pharm.*, 26:2(2000)167-176.

Follonier, N., et al, "Hot-Melt Extruded Pellets for the Sustained Release of Highly Dosed Freely Soluble Drugs," *Proceed. Intern. Symp. Control. Release Bioactive Materials*, 18(1991)578-579.

Forster, A., et al., "Characterization of Glass Solutions of Poorly Water-Soluble Drugs Produced by Melt Extrusion with Hydrophilic Amorphous Polymers," *J. Pharmacy Pharmacology*, 53(2001)303-315.

Foulds. G., et al., "The Absence of an Effect of Food on the Bioavailability of Azithromycin Administered as Tablets, Sachet or Suspension," *J. Antimicrobial Chemotherapy*, 37:Suppl. C(1996)37-44.

Gattefosse, "Gelucire® —Pharmaceutical Excipients for Oral Semi-Solid Formulations," Technical Dossier, 2$^{nd}$ edition, Gattefosse s.a., Cedex, France (1996).

Ghali, E.S., et al., "Thermal Treatment of Beads with Wax for Controlled Release," *Drug Development and Industrial Pharmacy*, 15:9(1989)1311-1328.

Hancock, B.C., and G. Zografi, "The Relationship Between the Glass Transition Temperature and the Water Content of Amorphous Pharmaceutical Solids," *Pharmaceutical Research*, 11:4(1994)471-477.

Joachim, J., et al., "Le Compritor, Etudes Galenique, Physique et Statstique," *APGI*, IV(1989)291-296.

Johnson, D.E., et al., "A New Method for Coating Glass Beads for Use in Gas Chromatography of Chloropromazine and Its Metabolites," Source unknown, and date unknown. (May be 1964-1965).

Jorgensen, K., et al., "Dissolution Stability of Multiparticulate Controlled Release Tablets," *Int'l J. Pharmaceutics*, 153(1997)1-11 .

Meshall, M.M., et al., "Optimization of Theophylline Release from Tablets Containing Compritol," *S.T.P. Pharma Sciences*, 5:6(1995)429-434.

Perez, M. deLos A, et al., "Sustained Release Phenylpropanolamine Hydrochloride from Compritol ATO-888 Matrix," *Pharmaceutical Research*, 9:10(1992)S-162, Abstract No. PT6191.

Perez, M.A., et al., "Sustained Release Phenylpropanolamine Hydrochloride from ATO 888 Matrix," PRHSJ, 12:4(1993)263-267.

Perissutti, B., et al., "Solid Dispersions of Carbamazepine with Getucire 44/14 and 50/13," *S.T.P. Pharma Sciences*, 10:6(2000)479-484.

Physician's Desk Reference, Information cited on Zithromax® capsules (equivalent to 250 mg azithromycin), tablets (equivalent to 600 mg azithromycin), and oral suspension (equivalent to 1 g azithromycin).

Reilly, W.J. Jr., and J.B. Schwartz, "A Potential Controlled Release Wax Matrix Excipient," *Pharmaceutical Research*, 8:10(1991)98, supplement, Abstract No. PT6108.

Reis, R. and F. Moll, "Matrix Formation of Polyglycolic Acid Tablets by Annealing," *European J. Pharm. and Biopharm.*, 40:1(1994)14-18.

Rxlist.com, "Azithromycin," description of drug, categories, brand names, from Internet website, Mar. 14, 2001.

San Vincente, A., et al., "Effect of Aging on the Release of Salbutamol Sulfate from Lipid Matrices," *Int'l J. Pharmaceutics*, 208(2000)13-21).

Schwartz, J.B., et al., "A Potential Controlled Release Wax Matrix Excipient for Tablets," *Pharmaceutical Research*, 9:10(1992)S-162, Abstract No. PT6189.

Schwartz, J.B., et al., Preliminary Evaluation of Controlled Release Agents for Tablets, *Pharmaceutical Research*, 9:10(1992)S-162, Abstract No. PT6190.

Sugao, H., et al, "Taste Masking of Bitter Drug Powder without Loss of Bioavailability by Heat Treatment of Wax-Coated Microparticles," *J. Pharmaceutical Sci.*, 87:1(1998)96-100.

Thomsen, L.J., et al., "Prolonged Release Matrix Pellets Prepared by Melt Pelletization. I. Process Variables," *Drug Development and Industrial Pharmacy*, 19:15(1993)187-1887.

Wang, A.E. and J.B. Schwartz, "Effect of Temperature on Drug Release from Wax Matrix Tablets After Thermal Treatment," *Pharmaceutical Research*, 11:10(1994)S-155, Abstract No. 6099.

Zhang, Y.-E., et al., Effect of Processing Methods and Heat Treatment on the Formation of Wax Matrix Tablets for Sustained Drug Release, *Pharm. Dev. Technol.*, 6:2(2001)131-144.

Arguendas, A., "Single Dose Therapy in Otitis Media, *Clinical Microbiology and Infection*," Abstract, S130, vol. 5, Supplemental 3, (1999).

Block, S., et al., "Single-Dose Azithromycin (30 mg/kg) in Acute Otitis Media," ICAAC, New Orleans, LA, Sep. 7-10, 2003, Abstract 174.

Curatolo, W., et al., "Site-Specific Absorption and Toleration of Azithromycin," Proceedings Intern. Symposium Rel. Bioact. Mater., 23, 1996.

Luke, D.R., et al, "Clinical Pharmacology of Azithromycin Given at Various Sites Along the Gastrointestinal Tract in Healthy Subjects," pp. 464-468.

Physicians Desk Reference, "*Appendix A Summary of Pediatric Suspension Commercial Products*," 55$^{th}$ edition, Phase III Clinical Dosage Form Nomination, pp. 19 and 28 (2001).

Pfizer, Inc., Zithromax [package insert], "Zithromax (azithromycin tablets) and (azithromycin for oral suspension)," www.pfizer.com/download/uspi_zithromax.pdf (2004).

\* cited by examiner

EXTRUSION PROCESS FOR FORMING CHEMICALLY STABLE DRUG MULTIPARTICULATES

The present application claims the priority benefit of U.S. Provisional Application No. 60/527,315, filed on Dec. 4, 2003. The contents of the priority document are herein incorporated by reference.

BACKGROUND OF THE INVENTION

Multiparticulates are well-known dosage forms that comprise a multiplicity of particles whose totality represents the intended therapeutically useful dose of a drug. When taken orally, multiparticulates generally disperse freely in the gastrointestinal tract, maximize absorption, and minimize side effects. See, for example, *Multiparticulate Oral Drug Delivery* (Marcel Dekker, 1994), and *Pharmaceutical Pelletization Technology* (Marcel Dekker, 1989).

A typical multiparticulate formulation consists of a drug substantially uniformly distributed in a carrier. A conventional process for producing such multiparticulates is to add the drug and carrier to a heated tank to produce a molten mixture that is then atomized into droplets and the droplets congealed to form the multiparticulates. This process is capable of forming small, round, smooth multiparticulates in which the drug is encapsulated in the carrier. However, conventional pharmaceutical manufacturing processes typically require a mean residence time of the drug in the molten mixture of several hours or longer for economical production of the multiparticulates. For some drugs, such long mean residence times can lead to rapid drug degradation or to undesirable reactions of the drug with the carrier. Because of this, conventional pharmaceutical melt-congeal processes are not considered useful for preparing multiparticulates of labile drugs.

It is also known to form multiparticulates using other processes which do not form a molten mixture, such as extrusion spheronization or wet granulation. However, such processes often result in multiparticulates in which the drug is not completely encapsulated in the carrier. Moreover, such processes may result in multiparticulates that have irregular or rough exterior surfaces. Such multiparticulates may have poor flow properties and may be difficult to coat. In addition, irregular and rough multiparticulates present a gritty sensation in the mouth.

U.S. Pat. Nos. 6,261,599 and 6,335,033 disclose a controlled release dosage form comprising an opioid analgesic and a carrier. The analgesic and carrier are blended and then heated to a temperature sufficiently high to extrude the blend into a strand having a diameter of from 0.1 to 3 mm. The strand is then cooled and divided to form multiparticulates. There is no disclosure of the use of an atomizer to form multiparticulates from the extrudate, nor is there any recognition of improved chemical stability obtained by using an extruder to form the molten mixture.

U.S. Pat. No. 6,248,363 discloses a spray-congeal process for forming free-flowing drug-containing powders from melts. The drug is allowed to melt, disperse, or dissolve in a hot melt of a carrier and is then atomized into an air chamber wherein the temperature is below the melting point of the components, thereby providing spherical congealed pellets. The process is stated to be suitable for heat labile substances since ambient temperature is used to dry the pellets. However, there is no disclosure of the use of an extruder to produce a molten mixture to be atomized, nor is the need for minimizing the mean residence of the drug in the molten mixture to improve chemical stability.

U.S. Pat. No. 5,824,342 discloses solloids consisting of a solid suspension of a solid non-fat substrate having an active ingredient associated therewith, the non-fat substrate and the active being non-uniformly dispersed in a solid fat carrier. The solloids may be made by a "flash shear" process wherein the temperature of a feedstock material is raised to a point where the carrier undergoes intraparticle flow. The flash shear process is stated to be a "cold flow" process that has no long residence times in the carrier and so avoids the problems associated with a heat history created by long residence times.

U.S. Pat. No. 6,139,872 discloses an extrusion process for producing a nutritional supplement powder consisting of forming a feedstock into a plastic mass that is not completely molten, then shaping, cooling and comminuting the plastic mass to obtain the powder.

U.S. Pat. No. 5,100,592 discloses a process for forming particles from a powdery material wherein the powdery material is discharged onto a heated rotary spreader. A portion of the powdery material is melted on the rotary spreader, coating non-melted particles, which are then discharged as larger particles from the periphery of the rotary spreader.

U.S. Pat. No. 4,086,346 discloses a method for melt-spraying the thermally sensitive drug phenacetin alone by means of a multi-screw extruder having extremely tight clearances between the screw shafts and between the screws and the housing, the extruder melting the drug, delivering the molten drug to an atomizer for atomizing and cooling and solidifying the melt-sprayed drug.

U.S. Pat. No. 5,766,521 discloses a process for melt-congealing crystallized pearls of the drug glyceryl guaiacolate, whereby the drug is melted, atomized, then cooled to below the drug's glass transition temperature to form pearls, placing the so-formed pearls into contact with crystallization seeds and then crystallizing the pearls by heating.

Published U.S. Patent Application No. 2001/0006650 discloses solid solution beadlets of drug, a fatty acid or ester and a surfactant formed by spray-congealing, consisting of mixing drug particles in the melted fatty acid or ester, then spraying the resulting mixture into a spray-congeal tower having cool air flowing through the tower to solidify the beadlets. However, there is no disclosure of the use of an extruder to form a drug/carrier molten mixture, nor any suggestion of a solution to the problem of degradation of labile drugs used in the process.

There is therefore a need in the art for an efficient melt-congeal process of forming multiparticulates containing labile drugs wherein drug degradation is kept to an acceptably low level during the process, and which results in multiparticulates that are smooth, round, and in which the drug is substantially encapsulated in the carrier.

BRIEF SUMMARY OF THE INVENTION

The inventors have discovered that the drawbacks of prior art melt-congeal processes can be overcome by use of an extruder in combination with an atomizer, such as a spinning-disk atomizer. In this process, a molten mixture, comprising a labile drug and a carrier is formed using an extruder, such as a twin-screw extruder. The molten mixture is directed to an atomizer to produce droplets of the molten feed. The droplets are congealed to form multiparticulates. This process has the advantage of reducing drug degradation of labile drugs while at the same time forming multiparticulates that have good physical characteristics. The use of the extruder to form the molten mixture reduces the amount of time during which the drug is exposed to high temperatures relative to the conventional method that uses a heated tank. Nevertheless, by delivering a molten mixture to an atomizer, the process is capable of forming small, round, smooth multiparticulates in which the drug is substantially encapsulated in the carrier.

The multiparticulates formed by the process of the present invention may be for immediate, sustained, delayed or controlled release of drug after introduction to a use environment. As used herein, a "use environment" can be either the in vivo environment of the GI tract of an animal such as a mammal or human, or the in vitro environment of a test solution. Exemplary test solutions include aqueous solutions at 37° C. comprising (1) 0.1 N HCl, simulating gastric fluid without enzymes; (2) 0.01 N HCl, simulating gastric fluid that avoids excessive acid degradation of azithromycin, and (3) 50 mM $KH_2PO_4$, adjusted to pH 6.8 using KOH or 50 mM $Na_3PO_4$, adjusted to pH 6.8 using NaOH, both of which simulate intestinal fluid without enzymes. The inventors have also found that for some formulations, an in vitro test solution comprising 100 mM $Na_2HPO_4$, adjusted to pH 6.0 using NaOH provides a discriminating means to differentiate among different formulations on the basis of dissolution profile. It has been determined that in vitro dissolution tests in such solutions provide a good indicator of in vivo performance and bioavailability. Further details of in vitro tests and test solutions are described herein.

Detailed guidelines on selection of processing conditions, carriers and their interrelationships are set forth in the Detailed Description of Preferred Embodiments below.

DETAILED DESCRIPTION OF PREFERRED EMBODIMENTS

The compositions formed by the process of the present invention comprise a plurality of drug-containing "multiparticulates." The term "multiparticulate" is intended to embrace a dosage form comprising a multiplicity of particles whose totality represents the intended therapeutically useful dose of the drug in question. The particles generally are of a mean diameter from about 40 to about 3000 μm, preferably 50 to 1000 μm, and most preferably 100 to 300 μm. Multiparticulates are advantageous drug forms because they are amenable to use in scaling dosage forms according to the weight of an individual animal in need of treatment by simply scaling the mass of particles in the dosage form to comport with the animal's weight. They are further advantageous since they allow the incorporation of a large quantity of drug into a simple dosage form such as a sachet that can be formulated into a slurry that can easily be consumed orally. Multiparticulates also have numerous therapeutic advantages over other dosage forms, especially when taken orally, including (1) improved dispersal in the gastrointestinal (GI) tract, (2) relatively rapid and reproducible passage from the stomach, (3) more uniform GI tract transit time, and (4) reduced inter- and intra-patient variability. As used herein, the term "about" means±10% of the value.

While the multiparticulates can have any shape and texture, it is preferred that they be spherical, with a smooth surface texture. These physical characteristics lead to excellent flow properties, improved "mouth feel," ease of swallowing and ease of uniform coating, if required.

Melt-Congeal Process

The basic process of the present invention comprises the steps of (a) forming in an extruder a molten mixture comprising a labile drug and a pharmaceutically acceptable carrier,
(b) delivering the molten mixture of step (a) to an atomizing means to form droplets from the molten mixture, and
(c) congealing the droplets from step (b) to form multiparticulates.

The molten mixture comprises a labile drug and a pharmaceutically acceptable carrier, defined in detail below. "Molten mixture" means that the mixture of drug and carrier is sufficiently heated by extrusion to fluidize the mixture sufficiently to atomize it or form it into droplets. Atomization of the molten mixture may be carried out using any of the atomization methods described below. Generally, the mixture is molten in the sense that it will flow when subjected to one or more forces such as pressure, shear, and centrifugal force, such as that exerted by a centrifugal or spinning-disk atomizer. Thus, the drug/carrier mixture may be considered "molten" when any portion of the carrier and/or drug becomes sufficiently fluid that the mixture, as a whole, may be atomized. Generally, a mixture is sufficiently fluid for atomization when the viscosity of the molten mixture is less than about 20,000 cp, preferably less than about 15,000 cp, more preferably less than about 10,000 cp. Often, the mixture becomes molten when the mixture is heated by extrusion above the melting point of the drug or one or more of the carrier components, in cases where the carrier is sufficiently crystalline to have a relatively sharp melting point. When the carrier components are amorphous, the mixture becomes molten when its temperature rises above the softening point of one or more of the carrier components.

Thus, the molten mixture may comprise (1) drug dissolved in the molten carrier, (2) drug suspended in the molten carrier, (3) carrier suspended in the molten drug, (4) molten drug suspended in the molten carrier, or (5) any combination of such states or those states that lie between. In one preferred embodiment, the molten mixture comprises substantially crystalline drug particles suspended in the molten carrier. In such cases, a portion of the drug may be dissolved in the fluid carrier and a portion of the carrier may remain solid. Preferably, less than about 30 wt % of the total drug melts or dissolves in the molten carrier.

The molten mixture is formed in an extruder. By "extruder" is meant a device or collection of devices that creates a molten extrudate by heat and/or shear forces and/or produces a uniformly mixed extrudate from a solid and/or liquid (e.g., molten) feed. Such devices include, but are not limited to single-screw extruders; twin-screw extruders, including co-rotating, counter-rotating, intermeshing, and non-intermeshing extruders; multiple screw extruders; ram extruders, consisting of a heated cylinder and a piston for extruding the molten feed; gear-pump extruders, consisting of a heated gear pump, generally counter-rotating, that simultaneously heats and pumps the molten feed; and conveyer extruders. Conveyer extruders comprise a conveyer means for transporting solid and/or powdered feeds, such, such as a screw conveyer or pneumatic conveyer, and a pump. At least a portion of the conveyer means is heated to a sufficiently high temperature to produce the molten mixture. The molten mixture may optionally be directed to an accumulation tank, before being directed to a pump, which directs the molten mixture to an atomizer. Optionally, an in-line mixer may be used before or after the pump to ensure the molten mixture is substantially homogeneous. In each of these extruders the molten mixture is mixed to form a uniformly mixed extrudate. Such mixing may be accomplished by various mechanical and processing means, including mixing elements, kneading elements, and shear mixing by backflow. Thus, in such devices, the composition is fed to the extruder, which produces a molten mixture that can be directed to the atomizer.

In one embodiment, the drug/carrier mixture is fed to the extruder in the form of a solid powder. The powdered feed can be prepared using methods well known in the art for obtaining powdered mixtures with high content uniformity (e.g., as described in *Remington's Pharmaceutical Sciences,* 16th ed. 1980). Generally, it is desirable that the particle sizes of the drug and carrier be similar to obtain a uniform blend. However, this is not essential to the successful practice of the invention.

An example of a process for preparing a solid powder feed is as follows: first, the carrier is milled so that its particle size is about the same as that of the drug; next, the drug and carrier are blended in a V-blender for 20 minutes; the resulting blend is then de-lumped to remove large particles, then finally blended for an additional 4 minutes. In some cases it is difficult to mill the carrier to the desired particle size since many of these materials tend to be waxy substances and the heat generated during the milling process can gum up the milling equipment. In such cases, small particles of the carrier alone can be formed using a melt-congeal process, as described below. The resulting congealed particles of carrier can then be blended with the drug to produce the feed for the extruder.

A two-feed extruder system can also be used to produce the molten mixture. In this system the carrier and drug are fed to the extruder through the same or different feed ports. In this way, the need for blending the components is eliminated.

Alternatively, the carrier in solid form may be fed to the extruder at one point, allowing the extruder to melt the carrier. The drug is then added to the molten carrier through a second feed delivery port part way along the length of the extruder, thus reducing the residence time of the drug in the molten carrier. The closer the second feed delivery port is to the extruder discharge, the lower is the residence time of drug in the molten mixture. Multiple-feed extruders can be used when the carrier comprises more than one excipient.

In another method, the carrier can be first melted in, for example, a tank, and fed to the extruder in molten form. The drug, typically in solid form, may then be introduced to the extruder through the same or a different delivery port used to feed the carrier into the extruder. This system has the advantage of separating the melting step for the carrier from the mixing step.

In each of the above methods, the extruder should be designed so that it produces a molten mixture, preferably with drug crystals distributed substantially uniformly in the carrier. Generally, the temperature of the extrudate should be about 10° C. or more above the temperature at which the drug and carrier mixture becomes fluid. In cases where the carrier is a single crystalline material, this temperature is typically about 10° C. or more above the melting point of the carrier. The various zones in the extruder should be heated to appropriate temperatures to obtain the desired extrudate temperature as well as the desired degree of mixing or shear, using procedures well known in the art.

When the drug is in the form of a hydrate or solvate or when the drug comprises a co-species that is volatile (e.g., an HCl salt form), the drug can be maintained in this form by ensuring that the activity of volatile co-species in the molten mixture is sufficiently high that the volatile co-species is not removed from the drug by dissolution into the molten mixture. To keep the activity of volatile co-species in the carrier high, it is desirable to keep the gas phase atmosphere above the molten mixture at a high volatile co-species activity. This can be accomplished by adding the volatile co-species to the powdered feed blend, by injecting the volatile co-species (typically in liquid form) directly into the extruder through a separate delivery port, or by both. In either case, sufficient volatile co-species is added to ensure the activity is high enough to maintain the desired crystalline form of the drug. This is disclosed more fully in commonly assigned U.S. Patent Application Ser. No. 60/527,316 ("Method for Making Pharmaceutical Multiparticulates," Attorney Docket No. PC25021), filed concurrently herewith.

Once the molten mixture has been formed, it is delivered to an atomizer that breaks the molten mixture into small droplets. Virtually any method can be used to deliver the molten mixture to the atomizer, including the use of pumps and various types of pneumatic devices such as pressurized vessels or piston pots. The extruder itself can be used to deliver the molten mixture to the atomizer. Typically, the molten mixture is maintained at an elevated temperature during delivery to the atomizer to prevent its solidification and to keep it flowing.

Generally, atomization occurs in one of several ways, including (1) by "pressure" or single-fluid nozzles; (2) by two-fluid nozzles; (3) by centrifugal or spinning-disk atomizers, (4) by ultrasonic nozzles; and (5) by mechanical vibrating nozzles. Detailed descriptions of atomization processes can be found in Lefebvre, *Atomization and Sprays* (1989) or in *Perry's Chemical Engineers' Handbook* (7th Ed. 1997).

There are many types and designs of pressure nozzles, which generally deliver the molten mixture at high pressure to an orifice. The molten mixture exits the orifice as a filament or as a thin sheet that breaks up into filaments, which subsequently break up into droplets. The operating pressure drop across the pressure nozzle ranges from 1 barg to 70 barg, depending on the viscosity of the molten mixture, the size of the orifice, and the desired size of the multiparticulates.

In two-fluid nozzles, the molten mixture is contacted with a stream of gas, typically air or nitrogen, flowing at a velocity sufficient to atomize the molten mixture. In internal-mixing configurations, the molten mixture and gas mix inside the nozzle before discharging through the nozzle orifice. In external-mixing configurations, high velocity gas outside the nozzle contacts the molten mixture. The pressure drop of gas across such two-fluid nozzles typically ranges from 0.5 barg to 10 barg.

In centrifugal atomizers, also known as rotary atomizers or spinning-disk atomizers, the molten mixture is fed onto a rotating surface, where it is caused to spread out by centrifugal force. The rotating surface may take several forms, examples of which include a flat disk, a cup, a vaned disk, and a slotted wheel. The surface of the disk may also be heated to aid in formation of the multiparticulates. Several mechanisms of atomization are observed with flat-disk and cup centrifugal atomizers, depending on the flow of molten mixture to the disk, the rotation speed of the disk, the diameter of the disk, the viscosity of the feed, and the surface tension and density of the feed. At low flow rates, the molten mixture spreads out across the surface of the disk and when it reaches the edge of the disk, forms a discrete droplet, which is then flung from the disk. As the flow of molten mixture to the disk increases, the mixture tends to leave the disk as a filament, rather than as a discrete droplet. The filament subsequently breaks up into droplets of fairly uniform size. At even higher flow rates, the molten mixture leaves the disk edge as a thin continuous sheet, which subsequently disintegrates into irregularly sized filaments and droplets. The diameter of the rotating surface generally ranges from 2 cm to 50 cm, and the rotation speeds range from 500 rpm to 100,000 rpm or higher, depending on the desired size of the multiparticulates, the properties of the molten mixture and the flow rate to the atomizer.

In ultrasonic nozzles, the molten mixture is fed through or over a transducer and horn, which vibrates at ultrasonic frequencies, atomizing the molten mixture into small droplets. In mechanical vibrating nozzles, the molten mixture is fed through a needle vibrating at a controlled frequency, atomizing the molten mixture into small droplets. In both cases, the particle size produced is determined by the liquid flow rate, frequency of ultrasound or vibration, and the orifice diameter.

In a preferred embodiment, the atomizer is a centrifugal or spinning-disk atomizer, such as the FX1 100-mm rotary atomizer manufactured by Niro A/S (Soeborg, Denmark).

The drug and carrier are delivered to the atomization step of the process as a molten mixture. Preferably, the mean residence time for drug in the molten mixture prior to congealing is at least 5 seconds, more preferably at least 10 seconds, and most preferably at least 15 seconds, so as to ensure the drug is substantially uniformly distributed in the molten mixture. It is also preferred that the mean residence time of drug in the molten mixture be no more than about 20 minutes to limit drug degradation reactions such as oxidation, reduction, esterification, transesterification, hydrolysis, lactonization or ring cyclization. Depending on the reactivity of the drug, it may be preferable to further reduce the time that the drug is in the molten mixture to well below 20 minutes in order to keep drug degradation to an acceptable level. In such cases, it may be preferable that such mixtures are molten for less than 15 minutes, and in some cases, even less than 10 minutes.

The mean residence time of material in an extruder can be determined by methods well known in the art. In one exemplary method, a small amount of dye or other similar compound is added to the feed while the extruder is operating under nominal conditions. The extrudate is then analyzed over time for the dye, from which the mean residence time of the dye in the extruder is determined.

Once the molten mixture has been atomized, the droplets are congealed, typically by contact with a gas or liquid at a temperature below the solidification temperature of the droplets. Typically, it is desirable that the droplets are congealed in less than about 60 seconds, preferably in less than about 10 seconds, more preferably in less than about 1 second. Often, congealing at ambient temperature results in sufficiently rapid solidification of the droplets. However, the congealing step often occurs in an enclosed space to simplify collection of the multiparticulates. In such cases, the temperature of the congealing medium (either gas or liquid) will increase over time as the droplets are introduced into the enclosed space, leading to possible drug degradation reactions. Thus, a cooling gas or liquid is often circulated through the enclosed space to maintain a constant congealing temperature.

Drugs

The multiparticulates formed by the process of the present invention comprise a labile drug and a carrier. As used herein the term "labile" refers to drugs that degrade by at least 0.01 wt % when held in a molten mixture of drug, carrier and optional excipient(s) for 60 minutes. Details on carriers and optional excipients are discussed below. The term "drug" as used herein includes, by way of example and not of limitation, any physiologically or pharmacologically active substance that produces a localized or systemic effect in animals. The term "animals" includes mammals, particularly humans, as well as other animals.

Preferably, the drug makes up from about 5 wt % to about 90 wt % of the total weight of the multiparticulate, more preferably from about 10 wt % to about 80 wt %, even more preferably from about 30 wt % to about 60 wt % of the total weight of the multiparticulates.

Before forming the multiparticulates, the drug can be amorphous or crystalline. Preferably, at least 70 wt % of the drug is crystalline, more preferably, at least 80 wt % of the drug is crystalline, even more preferably at least 90 wt % of the drug is crystalline, and most preferably at least 95 wt % of the drug is crystalline prior to forming the multiparticulates.

After forming multiparticulates by the process of the present invention, the drug may be amorphous or crystalline. Preferably, the drug in the multiparticulate is crystalline, including any crystalline polymorphs. A "major portion" of the drug in the multiparticulates can be crystalline, meaning that at least 70% of the drug is crystalline. The degree of drug crystallinity in the multiparticulates can be "substantially crystalline," meaning that the amount of crystalline drug in the multiparticulates is at least 80%, "almost completely crystalline," meaning that the amount of crystalline drug is at least 90%, or "essentially crystalline," meaning that the amount of crystalline drug in the multiparticulates is at least 95%.

The crystallinity of the drug in the multiparticulates may be determined using Powder X Ray Diffraction (PXRD) analysis. In an exemplary procedure, PXRD analysis may be performed on a Bruker AXS D8 Advance diffractometer. In this analysis, samples of about 500 mg are packed in Lucite sample cups and the sample surface smoothed using a glass microscope slide to provide a consistently smooth sample surface that is level with the top of the sample cup. Samples are spun in the $\phi$ plane at a rate of 30 rpm to minimize crystal orientation effects. The X-ray source (S/B $KCu_{\alpha}$, $\lambda$=1.54 Å) is operated at a voltage of 45 kV and a current of 40 mA. Data for each sample are collected over a period of about 20 to about 60 minutes in continuous detector scan mode at a scan speed of about 1.8 seconds/step to about 12 seconds/step and a step size of 0.02°/step. Diffractograms are collected over the $2\theta$ range of about 4° to 30°.

The crystallinity of the test sample is determined by comparison with two or more calibration standards consisting of physical mixtures of crystalline drug and carrier. Each physical mixture is blended together about 15 minutes on a Turbula mixer. Using the instrument software, the area under the diffractogram curve is integrated over the $2\theta$ range using a linear baseline. This integration range includes as many drug-specific peaks as possible while excluding carrier-related peaks. A linear calibration curve of percent crystalline drug versus the area under the diffractogram curve is generated from the calibration standards. The crystallinity of the test sample is then determined using these calibration results and the area under the curve for the test sample. Results are reported as a mean percent drug crystallinity (by crystal mass).

The crystalline form of a drug is generally preferred since it is more chemically stable than the amorphous form. This chemical stability arises from the fact that in crystalline form, drug molecules are locked into a rigid three-dimensional structure that is at a low thermodynamic energy state. Removal of a drug molecule from this structure, for example, to react with a carrier, will therefore take a considerable amount of energy. In addition, crystal forces reduce the mobility of the drug molecules in the crystal structure. The result is that the rate of degradation of crystalline drug is significantly reduced as compared to formulations containing amorphous drug.

Types of chemical degradation reactions that may occur in labile drugs to degrade them include, but are not limited to, hydrolysis, lactonization, esterification, oxidation, reduction, ring cyclization, and transesterification.

Labile drugs may be identified experimentally by determining whether the drug chemically reacts or degrades when held in the molten mixture of drug, carrier and optional excipients for 60 minutes. In general, drug degradation may be measured using any conventional method for measuring the purity or potency of drug in a pharmaceutical composition. For example, the purity or potency of the drug substance prior to formation of the molten mixture may be measured using high-performance liquid chromatography (HPLC) or other analytical techniques well known in the art. The molten mixture comprising the drug and carrier is then formed and the drug held in the molten mixture for 60 minutes. The purity or potency of the drug after being in the molten mixture for 60 minutes is then determined. A significant decrease in potency or purity indicates that a chemical reaction has occurred and is an indication of poor chemical stability.

An alternative method used to determine whether a drug is labile is to determine the concentration of a drug degradant(s) in the multiparticulate after being held in the molten mixture for 60 minutes. An increase in the concentration of a drug degradant(s) compared with the concentration present in the bulk drug substance would indicate reaction of the drug. An HPLC or other analytical technique may be used to determine the concentration of drug degradant(s).

These techniques may be used to determine a drug's "degree of degradation" after being held in the molten mixture for 60 minutes by subtracting the final percent drug purity (determined either by measuring the decrease in drug present or the increase in drug impurities present) from the initial percent drug purity. For example, a sample initially containing 100 mg drug and having no measurable impurities would have an initial percent drug purity of 100 wt %. If, after being held in the molten mixture for 60 minutes, the amount of drug in the sample decreases to 95 mg, the final percent drug purity would be 95 wt % and the degree of degradation would be 100 wt % less 95 wt %, or 5 wt %. Alternatively, if 100 mg of drug substance were found to initially have 2 mg of impurities present, it would have an initial percent drug purity of 98 wt %. If, after being held in the molten mixture for 60 minutes, the total impurities present had increased to 6 wt %, the final percent drug purity would be 94 wt % and the degree of degradation would be 98 wt % less 94 wt %, or 4 wt %.

Alternatively, degree of degradation can be determined by subtracting the amount of one or more specific drug degradant(s) initially present from the amount of the specific degradant(s) present after holding the drug in the molten mixture for 60 minutes. Such a measure is useful where there are several drug degradants, of which only one or a few is of concern. For example, if a drug initially contained a specific degradant at a concentration of 3 wt % and after being held in the molten mixture for 60 minutes the concentration of that degradant was 6 wt %, the degree of degradation would be 6 wt % less 3 wt %, or 3 wt %.

The need for the present invention will generally be greater when the drug's reactivity with or sensitivity to the molten mixture increases. The process of the present invention is preferred for labile drugs having a degree of degradation that is greater than 0.01 wt % after being held in the molten mixture for 60 minutes. Thus, the process of the present invention is preferred for labile drugs that have a degree of degradation of at least 0.05 wt %, more preferably at least 0.1 wt %, and most preferably at least 0.5 wt %.

The degree of degradation of a drug will depend on several factors, including (1) the chemical makeup of the drug, (2) the chemical makeup of the carrier, (3) other excipients used in the molten mixture, and (4) the temperature of the molten mixture. A drug may be labile when used in one multiparticulate formulation, but not in another formulation. For example, the crystalline dihydrate form of the drug azithromycin is labile, as defined above, when held in a molten mixture comprising 50 wt % azithromycin dihydrate, 47 wt % COMPRITOL 888 ATO (a mixture of glyceryl mono-, di-, and tribehenates available from Gattefossé Corporation, Paramus, New Jersey), and 3 wt % LUTROL F127 (poloxamer 407, a block copolymer of ethylene and propylene oxides, also known as PLURONIC F127 available from BASF Corporation, Mt. Olive, N.J.) at 90° C. for 60 minutes. Conversely, the same form of azithromycin is not labile when held for 60 minutes in a molten mixture comprising 50 wt % azithromycin dihydrate, 48 wt % microcrystalline wax, and 2 wt % LUTROL F127.

Examples of drugs employed in the multiparticulates made by the inventive process include, without limitation, inorganic and organic compounds that act on the peripheral nerves, adrenergic receptors, cholinergic receptors, nervous system, skeletal muscles, cardiovascular smooth muscles, blood circulatory system, synaptic sites, neuroeffector junctional sites, endocrine and hormone systems, immunological system, reproductive system, autocoid systems, alimentary and excretary systems, inhibitors of autocoids and histamine systems. Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesterol ester transfer protein inhibitors.

Each named drug should be understood to include the neutral form of the drug and pharmaceutically acceptable forms thereof. By "pharmaceutically acceptable forms" thereof is meant any pharmaceutically acceptable derivative or variation, including stereoisomers, stereoisomer mixtures, enantiomers, solvates, hydrates, isomorphs, polymorphs, salt forms and prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4',6'-trimethylphenoxy) pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin, amoxicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid, quinapril, and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R-(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesterol ester transfer protein inhibitors include [2R,4S]-4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S]-4-[3,5-bis-trifluoromethyl-benzyl)-methoxycarbonyl-amino]-2-ethyl-6-trifluoromethyl-3,4-dihydro-2H-quinoline-1-carboxylic acid ethyl ester, and [2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester.

A preferred drug for use with the present invention is azithromycin. Azithromycin is the generic name for the drug 9a-aza-9a-methyl-9-deoxo-9a-homoerythromycin A, a broad-spectrum antimicrobial compound derived from erythromycin A. Accordingly, azithromycin and certain derivatives thereof are useful as antibiotics. The azithromycin may be in the form of the free base, a pharmaceutically acceptable salt or a prodrug. The azithromycin may also be in its anhydrous, hydrated or solvated forms. The invention is intended to encompass all such forms. The azithromycin present in the multiparticulates of the present invention is preferably crystalline, including any crystalline polymorphs. The various polymorphs of crystalline azithromycin are disclosed in commonly assigned pending U.S. Patent Application Publication No. 20030162730, published Aug. 28, 2003; U.S. Pat. Nos. 6,365,574 and 6,245,903; U.S. Patent Application Publication Nos. 20010047089, published Nov. 29, 2001, and 20020111318, published Aug. 15, 2002; and International Application Publication Nos. WO 01/00640, WO 01/49697, WO 02/10181 and WO 02/42315. In a preferred embodiment, the azithromycin is in the form of the crystalline dihydrate, described in U.S. Pat. No. 6,268,489.

Reduced Levels of Degradation

The drug in the multiparticulates made by the inventive process has reduced levels of degradation compared with the same drug in control multiparticulates. The control multiparticulates are the same as those made by the inventive process with the exception that the time the drug is in the molten mixture is 60 minutes. The 60-minute time period was chosen as an appropriate control as it generally represents the shortest time a drug is in the presence of a molten mixture in an economical conventional melt-congeal process for forming drug multiparticulates.

A "relative degree of improvement in drug degradation" may be used to measure the reduced levels of degradation obtained using the inventive process. This measure is determined by dividing (i) the degree of degradation of the drug in the control multiparticulate by (ii) the degree of degradation of the drug in multiparticulate made by the inventive process. For example, where the degree of degradation of a drug in the control multiparticulate is 50 wt %, and the degree of degradation of multiparticulate made by the inventive process is 1 wt %, the relative degree of improvement is 50 wt %±1 wt %, or 50.

The multiparticulates made by the process of the present invention provide a measurable improvement in drug degradation of the drug relative to the control drug-containing multiparticulates. By "measurable improvement" in drug degradation is meant that the relative degree of improvement in drug degradation is at least 1.05. When the drug is particularly unstable, larger relative degrees of improvement may be necessary in order for the drug degradation of the multiparticulate to be pharmaceutically acceptable. In such cases, the inventive process provides reduced levels of drug degradation when the relative degree of improvement is at least about 1.10, preferably at least about 1.25, more preferably at least about 2, even more preferably at least about 5, and most preferably at least 10. In fact, some multiparticulates made by the inventive process may achieve a relative degree of improvement in drug degradation of greater than 100.

Carriers

The multiparticulates formed by the process of the present invention include a pharmaceutically acceptable carrier. By "pharmaceutically acceptable" is meant the carrier must be compatible with the other ingredients of the composition, and not be deleterious to the patient. The carrier functions as a matrix for the multiparticulate or to affect the rate of release of drug from the multiparticulate, or both. The carrier may be a single material or a mixture of two or more materials.

Carriers used in the process of the present invention will generally make up from about 10 wt % to about 95 wt % of the multiparticulate, preferably from about 20 wt % to about 90 wt %, and more preferably from about 40 wt % to about 70 wt % of the multiparticulate, based on the total mass of the multiparticulate. The carriers are preferably solid at temperatures of about 40° C. The inventors have found that if the carrier is not a solid at 40° C., there can be changes in the physical characteristics of the composition over time, especially when stored at elevated temperatures, such as at 40° C. Thus, it is preferred that the carrier be a solid at temperatures of about 50° C., and more preferably at about 60° C.

Exemplary carriers include waxes, such as synthetic wax, microcrystalline wax, paraffin wax, carnauba wax, and white and yellow beeswax; long-chain alcohols, such as stearyl alcohol, cetyl alcohol, and polyethylene glycol; long-chain fatty acid esters, also known as fats, such as glyceryl monooleate, glyceryl monostearate, glyceryl palmitostearate, polyethoxylated castor oil derivatives, hydrogenated vegetable oils, mono-, di-, and trialkyl glycerides, glyceryl monobehenate, glyceryl dibehenate, glyceryl tribehenate, glyceryl tristearate, glyceryl tripalmitate, and mixtures thereof.

Optional Excipients

The multiparticulates may optionally include excipients to aid in forming the multiparticulates, to affect the release rate of azithromycin from the multiparticulates, or for other purposes known in the art.

The multiparticulates may optionally include a dissolution enhancer. Dissolution enhancers increase the rate of dissolution of the drug from the carrier. In general, dissolution enhancers are amphiphilic compounds and are generally more hydrophilic than the carrier. Dissolution enhancers will generally make up about 0.1 to about 30 wt % of the total mass of the multiparticulate. Exemplary dissolution enhancers include alcohols such as stearyl alcohol, cetyl alcohol, and polyethylene glycol; surfactants, such as poloxamers (such as poloxamer 188, poloxamer 237, poloxamer 338, and poloxamer 407), docusate salts, polyoxyethylene alkyl ethers, polyoxyethylene castor oil derivatives, polysorbates, polyoxyethylene alkyl esters, sodium lauryl sulfate, and sorbitan monoesters; sugars such as glucose, sucrose, xylitol, sorbitol, and maltitol; salts such as sodium chloride, potassium chloride, lithium chloride, calcium chloride, magnesium chloride, sodium sulfate, potassium sulfate, sodium carbonate, magnesium sulfate, and potassium phosphate; amino acids such as alanine and glycine; and mixtures thereof. Preferably, the dissolution enhancer is a surfactant, and most preferably, the dissolution enhancer is a poloxamer.

Another useful class of excipients that may optionally be included in the multiparticulates include materials used to adjust the viscosity of the molten mixture used to form the multiparticulates. The viscosity of the molten mixture is a key variable in obtaining multiparticulates with a narrow particle size distribution. Viscosity-adjusting excipients will generally make up 0 to 25 wt % of the multiparticulate, based on the total mass of the multiparticulate. Generally, when a spinning-disk melt-congeal process is employed, it is preferred that the viscosity of the molten mixture be at least about 1 cp and less than about 10,000 cp, more preferably at least 50 cp and less than about 1000 cp. If the molten mixture has a viscosity outside these preferred ranges, a viscosity-adjusting excipient can be added to obtain a molten mixture within the preferred viscosity range. Examples of viscosity-reducing excipients include stearyl alcohol, cetyl alcohol, low molecular weight polyethylene glycol (less than about 1000 daltons), isopropyl alcohol, and water. Examples of viscosity-increasing excipients include microcrystalline wax, paraffin wax, synthetic wax, high molecular weight polyethylene glycols (greater than about 5000 daltons), colloidal silicon dioxide, magnesium silicate, sugars, and salts.

Other excipients may be added to adjust the release characteristics of the multiparticulates or to improve processing and will typically make up 0 to 50 wt % of the multiparticulate, based on the total mass of the multiparticulate. For example, acids or bases may be used to slow or speed the release of the drug, depending on the nature of the drug and other excipients. Examples of bases that can be included in the composition include di- and tri-basic sodium phosphate, di- and tri-basic calcium phosphate, mono-, di-, and tri-ethanolamine, sodium bicarbonate, sodium citrate dihydrate, amine-functionalized methacrylate polymers and copolymers, such as EUDRAGIT E100 from Rohm GmbH, as well as other oxide, hydroxide, phosphate, carbonate, bicarbonate and citrate salts, including various hydrated and anhydrous forms known in the art.

Still other excipients may be added to reduce the static charge on the multiparticulates; examples of such anti-static agents include talc and colloidal silicon dioxide.

Flavorants, colorants, and other excipients may also be added in their usual amounts for their usual purposes.

In one embodiment, the carrier and one or more optional excipients form a solid solution, meaning that the carrier and one or more optional excipients form a single thermodynamically stable phase. In such cases, excipients that are not solid at a temperature of less than about 40° C. can be used, provided the carrier/excipient mixture is solid at a temperature of up to about 40° C. This will depend on the melting point of the excipients used and the relative amount of carrier included in the composition. Generally, the greater the melting point of one excipient, the greater the amount of a low-melting-point excipient that can be added to the composition while still maintaining a carrier in a solid phase at 40° C.

In another embodiment, the carrier and one or more optional excipients do not form a solid solution, meaning that the carrier and one or more optional excipients form two or more thermodynamically stable phases. In such cases, the carrier/excipient mixture may be entirely molten at processing temperatures used to form multiparticulates or one material may be solid while the other(s) are molten, resulting in a suspension of one material in the molten mixture.

When the carrier and one or more optional excipients do not form a solid solution but one is desired, for example, to obtain a specific controlled-release profile, a third excipient may be included in the composition to produce a solid solution comprising the carrier, the one or more optional excipients, and the third excipient. For example, it may be desirable to use a carrier comprising microcrystalline wax and a poloxamer to obtain a multiparticulate with the desired release profile. In such cases a solid solution is not formed, in part due to the hydrophobic nature of the microcrystalline wax and the hydrophilic nature of the poloxamer. By including a small amount of a third component, such as stearyl alcohol, in the formulation, a solid solution can be obtained resulting in a multiparticulate with the desired release profile.

It is preferred that the drug have a low solubility in the carrier where solubility is defined as the mass of drug dissolved in the carrier divided by the total mass of carrier and dissolved drug at the processing conditions at which the molten mixture is formed. Low solubility will limit the formation of amorphous drug during the multiparticulate formation process. Preferably, the solubility of drug in the carrier is less than about 20 wt %, more preferably less than about 10 wt % and even more preferably less than about 5 wt %. The solubility of drug in a carrier may be measured by slowly adding crystalline drug to a molten sample of the carrier and determining the point at which drug will no longer dissolve in the molten sample, either visually or through quantitative analytical techniques, such as light-scattering. Alternatively, an excess of crystalline drug may be added to a sample of the molten carrier to form a suspension. This suspension may then be filtered or centrifuged to remove any undissolved crystalline drug and the amount of drug dissolved in the liquid phase can be measured using standard quantitative techniques, such as by HPLC. When performing these tests, the activity of any volatile species in the carrier, atmosphere, or gas to which the drug is exposed should be kept sufficiently high so that the crystal form of the drug does not change during the test, as previously mentioned.

In one embodiment, the multiparticulate comprises about 20 to about 75 wt % drug, about 25 to about 80 wt % of a carrier, and about 0.1 to about 30 wt % of a dissolution enhancer based on the total mass of the multiparticulate.

In a preferred embodiment, the multiparticulate comprises about 35 wt % to about 55 wt % drug; about 40 wt % to about 65 wt % of an excipient selected from waxes, such as synthetic wax, microcrystalline wax, paraffin wax, carnauba wax, and beeswax; glycerides, such as glyceryl monooleate, glyceryl monostearate, glyceryl palmitostearate, polyethoxylated castor oil derivatives, hydrogenated vegetable oils, glyceryl mono-, di- or tribehenates, glyceryl tristearate, glyceryl tripalmitate; and mixtures thereof; and about 0.1 wt % to about 15 wt % of a dissolution enhancer selected from surfactants, such as poloxamers, polyoxyethylene alkyl ethers, polysorbates, polyoxyethylene alkyl esters, sodium lauryl sulfate, and sorbitan monoesters; alcohols, such as stearyl alcohol, cetyl alcohol, and polyethylene glycol; sugars such as glucose, sucrose, xylitol, sorbitol, and maltitol; salts such as sodium chloride, potassium chloride, lithium chloride, calcium chloride, magnesium chloride, sodium sulfate, potassium sulfate, sodium carbonate, magnesium sulfate, and potassium phosphate; amino acids such as alanine and glycine; and mixtures thereof.

In another exemplary preferred embodiment, the multiparticulates made by the process of the present invention comprise (a) crystalline drug; (b) a glyceride carrier having at least one alkylate substituent of at least 16 carbon atoms; and (c) a polyoxyethylene-polyoxypropylene block copolymer (poloxamer). At least 70 wt % of the drug in the multiparticulate is crystalline. The choice of these particular carrier excipients allows for precise control of the release rate of the drug over a wide range of release rates. Small changes in the relative amounts of the glyceride carrier and the poloxamer result in large changes in the release rate of the drug. This allows the release rate of the drug from the multiparticulate to be precisely controlled by selecting the proper ratio of drug, glyceride carrier and poloxamer. These matrix materials have the further advantage of releasing nearly all of the drug from the multiparticulate. Such multiparticulates are disclosed more fully in commonly assigned U.S. Patent Application Ser. No. 60/527329("Multiparticulate Crystalline Drug Compositions Having Controlled Release Profiles,", filed concurrently herewith.

Dosage Forms

Multiparticulates are amenable to use in scaling dosage forms according to the weight of an individual animal in need of treatment by simply scaling the mass of particles in the dosage form to comport with the animal's weight. The multiparticulates may be administered using any known dosage form, including: powders or granules that may be taken orally either dry or reconstituted by addition of water or other liquids to form a paste, slurry, suspension or solution; tablets; capsules; a unit dose packet, sometimes referred to in the art as a "sachet" or an "oral powder for constitution" (OPC); and pills. Various additives may be mixed, ground, or granulated with the compositions of this invention to form a material suitable for the above dosage forms.

The multiparticulates made by the inventive process are designed for immediate release, controlled release, delayed release, or sustained release of drug after introduction into a use environment. As used herein, a "use environment" can be either the in vivo environment of the GI tract, subdermal, intranasal, buccal, intrathecal, ocular, intraaural, subcutaneous, vaginal tract, arterial and venous blood vessels, pulmonary tract or intramuscular tissue of an animal, such as a mammal and particularly a human; or the in vitro environment of a test solution, such as a simulated gastric buffer (GB), a simulated intestinal buffer (IB), a phosphate buffered saline (PBS) solution, or a model fasted duodenal (MFD) solution.

The multiparticulates may also be post-treated to improve drug crystallinity and/or the stability of the multiparticulate. In one embodiment, the multiparticulates comprise a drug and a carrier, the carrier having a melting point of $T_m$° C.; the multiparticulates are treated by at least one of (i) heating the multiparticulates to a temperature of at least about 35° C. and less than about ($T_m$° C.–10° C.), and (ii) exposing the multiparticulates to a mobility-enhancing agent. This post-treatment step results in an increase in drug crystallinity in the multiparticulates, and typically in an improvement in at least one of the chemical stability, physical stability, and dissolution stability of the multiparticulates. Post-treatment processes are disclosed more fully in commonly assigned U.S. Patent Application Ser. No. 60/527245, ("Multiparticulate Compositions with Improved Stability," filed concurrently herewith.

Without further elaboration, it is believed that one of ordinary skill in the art can, using the foregoing description, utilize the present invention to its fullest extent. Therefore, the following specific embodiments are to be construed as merely illustrative and not restrictive of the scope of the invention. Those of ordinary skill in the art will understand that known variations of the conditions and processes of the following examples can be used.

EXAMPLES

Control C1

The inventors have found that azithromycin can form azithromycin esters by direct esterification and by transesterification when held in a melt containing a carrier having acid and/or ester substituents. Under these conditions, azithromycin is labile.

For Control C1, multiparticulates comprising 50 wt % azithromycin dihydrate, 45 wt % COMPRITOL 888 ATO and 5 wt % LUTROL F127 were made by first adding the components to a vessel and heating the contents to 90° C. with stirring to form the molten mixture. This molten mixture was held at 90° C. for 60 minutes. The molten mixture was then delivered to a spinning-disk atomizer at a rate of 140 g/min to form multiparticulates. The spinning disk atomizer, which was custom made, consists of a bowl-shaped stainless steel disk of 10.1 cm (4 inches) in diameter. The surface of the disk is heated with a thin film heater beneath the disk to about 90° C. That disk is mounted on a motor that drives the disk of up to approximately 10,000 RPM. The entire assembly is enclosed in a plastic bag of approximately 8 feet in diameter to allow congealing and to capture microparticulates formed by the atomizer. Air is introduced from a port underneath the disk to provide cooling of the multiparticulates upon congealing and to inflate the bag to its extended size and shape. The surface of the spinning disk atomizer was maintained at 90° C. and the disk was rotated at 5500 rpm while forming the azithromycin multiparticulates.

A suitable commercial equivalent to this spinning disk atomizer is the FX1 100-mm rotary atomizer manufactured by Niro A/S (Soeborg, Denmark).

The so-formed multiparticulates were then post-treated by placing them in a shallow tray at a depth of less than about 2 cm. This tray was then placed in a controlled-atmosphere oven at 40° C. and 75% RH for 5 days. Table 1 summarizes the conditions used to form the multiparticulates of Control C1.

Samples of the multiparticulates were analyzed for azithromycin esters by first extraction of the sample with methanol at a concentration of 1.25 mg azithromycin/mL and sonication for 15 minutes. The sample solutions were then filtered with a 0.45 μm nylon syringe filter. The sample solutions were then analyzed by HPLC using a Hypersil BDS C18 4.6 mm×250 mm (5 μm) HPLC column on a Hewlett Packard HP1100 liquid chromatograph. The mobile phase employed for sample elution was a gradient of isopropyl alcohol and 25 mM ammonium acetate buffer (pH approximately 7) as follows: initial conditions of 50/50 (v/v) isopropyl alcohol/ammonium acetate; the isopropyl alcohol percentage was then increased to 100% over 30 minutes and held at 100% for an additional 15 minutes. The flow rate was 0.80 mL/min. The method used a 75 μL injection volume and a 43° C. column temperature.

A Finnigan LCQ Classic mass spectrometer was used for detection. The atmospheric pressure chemical ionization (APCI) source was used in a positive ion mode with a selective ion-monitoring method. Azithromycin ester values were calculated from the MS peak areas based on an external azithromycin standard. The azithromycin ester values were reported as percentage of the total azithromycin in the sample. The results of this analysis are reported in Table 2 and show that the multiparticulates of Control C1 contained 0.52 wt % azithromycin esters, corresponding to a degree of degradation of 0.52 wt %. These data verify that azithromycin, when used in the formulation of Control C1, is labile.

Example 1

This example demonstrates that azithromycin-containing multiparticulates made by the process of the present invention result in reduced levels of azithromycin degradation.

Multiparticulates were made comprising 50 wt % azithromycin dihydrate, 45 wt % COMPRITOL 888 ATO, and 5 wt % LUTROL F127 using the process of the present invention. First, 4.75 kg azithromycin dihydrate, 4.275 kg of the COMPRITOL 888 ATO and 0.475 kg of the LUTROL F127 were blended in a twinshell blender for 20 minutes. This blend was then de-lumped using a Fitzpatrick L1A mill at 3000 rpm, knives forward using a 0.065-inch screen. The mixture was blended again in a twinshell blender for 20 minutes, forming a preblend feed.

The preblend feed was delivered to a Leistritz 27-mm twin-screw extruder (Model ZSE 27, American Leistritz Extruder Corporation, Somerville, N.J.), at a rate of 140 g/min, producing a molten mixture comprising a suspension of the azithromycin dihydrate in the COMPRITOL 888 ATO/LUTROL F127 at a temperature of about 90° C. The feed suspension was then delivered to the center of the spinning-disk atomizer used to form the multiparticulates of C1, heated to 90° C. and rotating at 5500 rpm.

The mean residence time of the azithromycin in the extruder was about 60 seconds and the total time the azithromycin was in the molten suspension was less than about 3 minutes and the total time the azithromycin was held in the molten mixture was less than about 5 minutes. The particles formed by the spinning-disk atomizer were congealed in ambient air and collected.

The properties of the melt-congealed microspheres such as particle size can be controlled by the viscosity of the melt and processing conditions. Given the combination of the materials in the preferred embodiments in the present invention, the viscosity of the melt is unchanged as long as the temperature of the heating system is kept at 90° C. The size of azithromycin multiparticulates can be controlled by the feed rate to the disk (the amount of molten materials fed into the spinning disk atomizer) and the disk speed. For example, particles with a diameter of about 200 μm can be formed by a combination of (1) feed rate at 8.4 kg/hr and disk speed at 5500 RPM or (2) feed rate at 20 kg/hr and disk speed at 5800 RPM, or (3) feed rate at 25 kg/hr and disk speed at 7100 RPM.

The conditions for forming the multiparticulates of Example 1 are summarized in Table 1.

The so-formed multiparticulates were post-treated as follows. Samples of the multiparticulates were placed in a shallow tray at a depth of about 2 cm. This tray was then placed in a controlled-atmosphere oven at 40° C. and 75% RH for 5 days.

Samples of the multiparticulates of Example 1 were analyzed for azithromycin esters as in Control C1. The results of this analysis are reported in Table 2 and show that the multiparticulates formed by the process of the present invention contained 0.04 wt % azithromycin esters, corresponding to a degree of degradation of 0.04 wt %. Thus, the process of the present invention resulted in a relative degree of improvement in drug degradation of 13 (0.52 wt %÷0.04 wt %) relative to Control C1.

Controls C2 and C3

For Controls C2 and C3, multiparticulates were made as in Control C1 with the exceptions noted in Table 1. The concentrations of azithromycin esters were determined as in Control 1 and are reported in Table 2. These results confirm that the azithromycin in the C2 and C3 formulations is labile.

Examples 2-3

These examples further demonstrate that the process of the present invention results in an improvement in drug degradation for azithromycin-containing multiparticulates.

Multiparticulates were made as in Example 1 comprising azithromycin dihydrate, COMPRITOL 888 ATO, and LUTROL F127 in various ratios with the variables noted in Table 1.

The concentration of azithromycin esters in the multiparticulates of Examples 2 and 3 were determined as in Control C1. The results of these tests are reported in Table 2 and show low concentrations of azithromycin esters. These data show that the multiparticulates of Examples 2 and 3 made by the process of the present invention provide a relative degree of improvement in drug degradation of 25 and 27 relative to Controls C2 and C3, respectively.

TABLE 1

| Ex. No. | Formulation Azithromycin/ COMPRITOL 888 ATO/LUTROL F127 (wt %) | Feed Rate (g/min) | Disk Speed (rpm) | Disk Temp (° C.) | Batch Size (g) | Post-treatment (° C./% RH; days) |
|---|---|---|---|---|---|---|
| C1 | 50/45/5 | 140 | 5500 | 90 | 20 | 40/75; 5 |
| 1 | 50/45/5 | 140 | 5500 | 90 | 9,500 | 40/75; 5 |
| C2 | 50/46/4 | 140 | 5500 | 90 | 20 | 40/75; 5 |
| 2 | 50.53/45.47/4 | 140 | 5500 | 89 | 9,700 | 40/75; 5 |
| C3 | 50/47/3 | 140 | 5500 | 90 | 20 | 40/75; 5 |
| 3 | 50/47/3* | 180 | 5500 | 86 | 1,015 | 40/75; 5 |

*3.45 wt % water added to pre-blend feed

TABLE 2

| Ex. No. | Ester Content (wt %) | Degree of Degradation (wt %) | Relative Degree of Improvement in Drug Degradation |
|---|---|---|---|
| C1 | 0.52 | 0.52 | — |
| 1 | 0.04 | 0.04 | 13 |
| C2 | 0.50 | 0.50 | — |
| 2 | 0.02 | 0.02 | 25 |
| C3 | 0.54 | 0.54 | — |
| 3 | 0.02 | 0.02 | 27 |

Azithromycin Release Rates From Examples 1-3

The azithromycin release rates from the multiparticulates of Examples 1-3 were determined using the following procedure. For Examples 1-2, a 750 mg sample of the multiparticulates was placed into a USP Type 2 dissoette flask equipped with Teflon-coated paddles rotating at 50 rpm. The flask contained 900 mL of 50 mM $Na_3PO_4$ buffer adjusted to pH 6.8 with NaOH, maintained at 37.0±0.5° C. The multiparticulates were pre-wet with 10 mL of the buffer before being added to the flask. A 3 mL sample of the fluid in the flask was then collected at 5, 15, 30, 60, 120, and 180 minutes following addition of the multiparticulates to the flask. The samples were filtered using a 0.45 μm syringe filter prior to analyzing via HPLC (Hewlett Packard 1100, Waters Symmetry $C_8$ column, 45:30:25 acetonitrile:methanol:25 mM $KH_2PO_4$ buffer at 1.0 mL/min, absorbance measured at 210 nm with a diode array spectrophotometer). The same procedure was used to evaluate the multiparticulates of Example 3, except that a 1048 mg sample of the multiparticulates was used, and the dissolution media was 50 mM $KH_2PO_4$ adjusted to pH 6.8 using KOH.

The results of these dissolution tests are reported in Table 3 and show the multiparticulates of Examples 1-3 exhibited controlled release of the azithromycin.

TABLE 3

| Ex. No. | Time (min) | Azithromycin Released (%) |
|---|---|---|
| 1 | 0 | 0 |
|  | 5 | 11 |
|  | 15 | 30 |
|  | 30 | 52 |
|  | 60 | 77 |
|  | 120 | 95 |
|  | 180 | 96 |
| 2 | 0 | 0 |
|  | 5 | 9 |
|  | 15 | 25 |
|  | 30 | 44 |
|  | 60 | 68 |
|  | 120 | 88 |
|  | 180 | 95 |
| 3 | 0 | 0 |
|  | 15 | 14 |
|  | 30 | 27 |
|  | 60 | 44 |
|  | 120 | 81 |
|  | 180 | 68 |

Example 4

Multiparticulates were made comprising 50 wt % azithromycin dihydrate, 47 wt % COMPRITOL 888 ATO, and 3 wt % LUTROL F127 using the following procedure. First, 140 kg azithromycin dihydrate was weighed and passed through a Quadro Comil 196S with a mill speed of 900 rpm. The mill was equipped with a No. 2C-075-H050/60 screen (special round, 0.075"), a No. 2F-1607-254 impeller, and a 0.225 inch spacer between the impeller and screen. Next, 8.4 kg of the LUTROL F127 and then 131.6 kg of the COMPRITOL 888 ATO were weighed and passed through a Quadro 194S Comil mill. The mill speed was set at 650 rpm. The mill was equipped with a No. 2C-075-R03751 screen (0.075"), a No. 2C-1601-001 impeller, and a 0.225-inch spacer between the impeller and screen. The milled mixture was blended using a Gallay 38 cubic foot stainless-steel bin blender rotating at 10 rpm for 40 minutes, for a total of 400 rotations, forming a preblend feed.

The preblend feed was delivered to a Leistritz 50 mm twin-screw extruder (Model ZSE 50, American Leistritz Extruder Corporation, Somerville, N.J.) at a rate of about 20 kg/hr. The extruder was operated in co-rotating mode at about 100 rpm, and interfaced with a melt/spray-congeal unit. The extruder had five segmented barrel zones and an overall extruder length of 20 screw diameters (1.0 m). Water was injected into barrel number 2 at a rate of 6.7 g/min (2 wt %). The extruder's rate of extrusion was adjusted so as to produce a molten feed suspension of the azithromycin dihydrate in the COMPRITOL 888 ATO/LUTROL F127 at a temperature of about 90° C.

The feed suspension was delivered to the spinning-disk atomizer of Example 1, rotating at 6400 rpm and maintained at a temperature of 90° C. The maximum total time the azithromycin was exposed to the molten suspension was less than 10 minutes. The particles formed by the spinning-disk atomizer were cooled and congealed in the presence of cooling air circulated through the product collection chamber. The mean particle size was determined to be about 200 μm using a Malvern particle size analyzer.

The so-formed multiparticulates were post-treated by placing a sample in a sealed barrel that was then placed in a controlled atmosphere chamber at 40° C. for 10 days. Samples of the post-treated multiparticulates were evaluated by PXRD, which showed that about 99% of the azithromycin in the multiparticulates was in the crystalline dihydrate form.

Samples of the multiparticulates of Example 4 were analyzed for azithromycin esters as in Control C1, which showed that the multiparticulates formed by the process of the present invention contained less than about 0.05 wt % azithromycin esters.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A process for the formation of chemically stable drug-containing multiparticulates comprising:

(a) forming in an extruder a molten mixture comprising a labile drug and a pharmaceutically acceptable carrier, wherein said carrier is selected from the group consisting of waxes, long-chain alcohols, long-chain fatty acid esters, and mixtures thereof, wherein said drug in said molten mixture is at least 70 wt % crystalline;

(b) delivering said molten mixture to an atomizing means to form droplets of said molten mixture; and (c) congealing said droplets to form multiparticulates.

2. The process of claim 1 wherein the mean time said drug is present in said molten mixture is greater than 5 seconds but less than or equal to 20 minutes.

3. The process of claim 2 wherein the mean time said drug is present in said molten mixture is greater than 10 seconds but less than or equal to 15 minutes.

4. The process of claim 3 wherein the mean time said drug is present in said molten mixture is greater than 10 seconds but less than or equal to 10 minutes.

5. The process of claim 1 wherein said extruder is selected from the group consisting of single-screw extruders, twin-screw extruders, multiple screw extruders, ram extruders, gear-pump extruders, and conveyer extruders.

6. The process of claim 1 wherein said atomizing means is selected from the group consisting of spinning disk atomizers, pressure nozzles, single-fluid nozzles, two-fluid nozzles, ultrasonic nozzles, and mechanical vibrating nozzles.

7. The process of claim 6 wherein said atomizing means is a spinning disk atomizer.

8. The process of claim 1 wherein said carrier is selected from the group consisting of synthetic wax, microcrystalline wax, paraffin wax, Carnauba wax, white and yellow beeswax, stearyl alcohol, cetyl alcohol, polyethylene glycol, glyceryl monooleate, glyceryl monostearate, glyceryl palmitostearate, hydrogenated vegetable oils, mono-, di-, and trialkyl glycerides, glyceryl monobehenate, glyceryl dibehenate, glyceryl tribehenate, glyceryl tristearate, glyceryl tripalmitate, and mixtures thereof.

9. The process of claim 1 wherein said molten mixture further includes a dissolution enhancer.

10. The process of claim 9 wherein said dissolution enhancer is selected from the group consisting of a alcohols, surfactants, sugars, salts, amino acids, and mixtures thereof.

11. The process of claim 10 wherein said dissolution enhancer is selected from the group consisting of stearyl alcohol, cetyl alcohol, polyethylene glycol poloxamers, docusate salts, polyoxyethylene alkyl ethers, polyoxyethylene castor oil derivatives, polysorbates, polyoxyethylene alkyl esters, sodium lauryl sulfate, sorbitan monoesters, glucose, sucrose, xylitol, sorbitol, maltitol, sodium chloride, potassium chloride, lithium chloride, calcium chloride, magnesium chloride, sodium sulfate, potassium sulfate, sodium carbonate, magnesium sulfate, potassium phosphate, alanine, glycine, and mixtures thereof.

12. The process of claim 11 wherein said carrier is a mixture of glyceryl mono-, di- and tribehenates and said dissolution enhancer is a poloxamer.

13. The process of claim 1 wherein said drug is selected from the group consisting of antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors. and cholesterol ester transfer protein inhibitors.

14. The process of claim 1 wherein said multiparticulates exhibit a relative degree of improvement in drug degradation of at least 1.05.

15. The process of claim 14 wherein said relative degree of improvement in drug degradation is at least 1.10.

16. The process of claim 15 wherein said relative degree of improvement in drug degradation is at least 1.25.

17. The process of claim 16 wherein said relative degree of improvement in drug degradation is at least 2.

18. The process of claim 17 wherein said relative degree of improvement in drug degradation is at least 5.

19. The process of claim 18 wherein said relative degree of improvement in drug degradation is at least 10.

* * * * *